United States Patent [19]

Trerotola

[11] Patent Number: 5,649,911
[45] Date of Patent: Jul. 22, 1997

[54] INTRAVENOUS CATHETER AND DELIVERY SYSTEM

[75] Inventor: Scott O. Trerotola, Carmel, Ind.

[73] Assignee: Indiana University Foundation, Bloomington, Ind.

[21] Appl. No.: 649,185

[22] Filed: May 17, 1996

[51] Int. Cl.⁶ .......................... A61M 5/32; A61M 5/178; A61M 5/00
[52] U.S. Cl. .......................... 604/164; 604/51; 604/165; 604/168
[58] Field of Search ...................... 604/51, 164, 165, 604/166, 167, 168

[56] References Cited

U.S. PATENT DOCUMENTS

| 2,001,638 | 5/1935 | Tornsjo | 604/165 |
|---|---|---|---|
| 3,492,992 | 2/1970 | Kurtz . | |
| 4,240,433 | 12/1980 | Bordow | 604/51 |
| 4,661,300 | 4/1987 | Daugherty . | |
| 4,664,657 | 5/1987 | Williamitis et al. | 604/265 |
| 4,680,029 | 7/1987 | Ranford et al. | 604/280 |
| 4,767,407 | 8/1988 | Foran | 604/164 |
| 5,215,528 | 6/1993 | Purdy et al. | 604/164 |
| 5,279,572 | 1/1994 | Hokama | 604/168 |
| 5,304,144 | 4/1994 | Brimhall | 604/177 |
| 5,306,253 | 4/1994 | Brimhall | 604/165 |
| 5,356,390 | 10/1994 | Erskine | 604/164 |
| 5,376,071 | 12/1994 | Henderson | 604/53 |
| 5,385,554 | 1/1995 | Brimhall | 604/168 |
| 5,409,461 | 4/1995 | Steinman | 604/110 |

OTHER PUBLICATIONS

Photographs of product "B D Whitacre Needle" marketed by Becton Dickinson and Company.

Primary Examiner—Sam Rimell
Assistant Examiner—Robert V. Racunas
Attorney, Agent, or Firm—Woodard, Emhardt, Naughton, Moriarty & McNett

[57] ABSTRACT

A catheter assembly comprising a needle received within a catheter. The needle has a solid tip and a hole in the cylindrical wall of the needle that communicates with the internal passageway of the needle. The needle is received within the lumen of the catheter, the catheter having a hole in its side wall that aligns with the side hole of the needle. Alignment of the side holes is provided by complementary alignment features on the proximal ends of the needle and catheter. The needle may be connected to a flash chamber for observation of fluid from the cavity. Fluid does not flow into the needle without first entering the side hole of the catheter. Observation of fluid in the flash chamber will not occur until the side hole of the catheter contacts the fluid. This side entrance provides positive indication that the distal end of the catheter has entered the cavity.

15 Claims, 9 Drawing Sheets

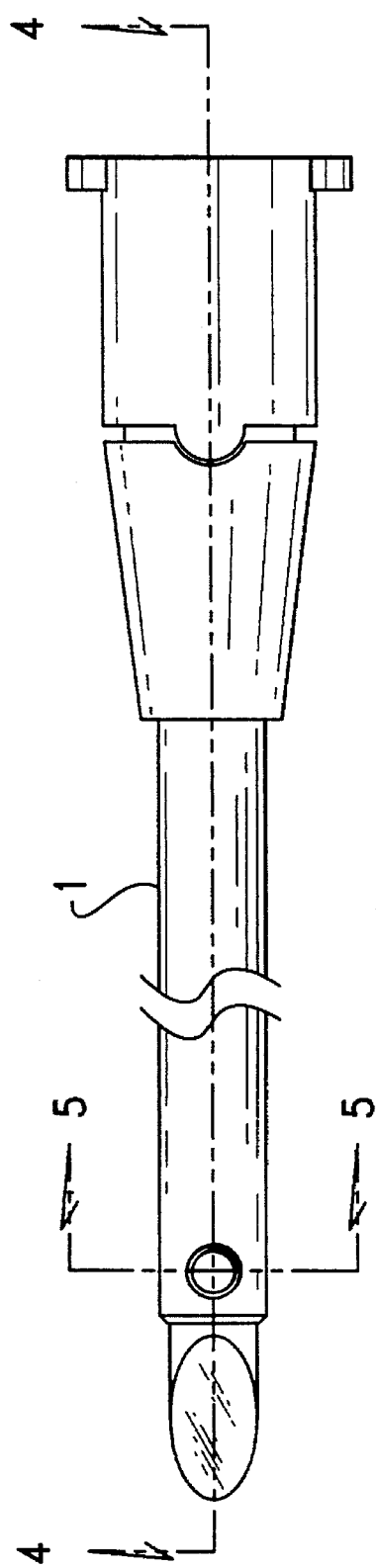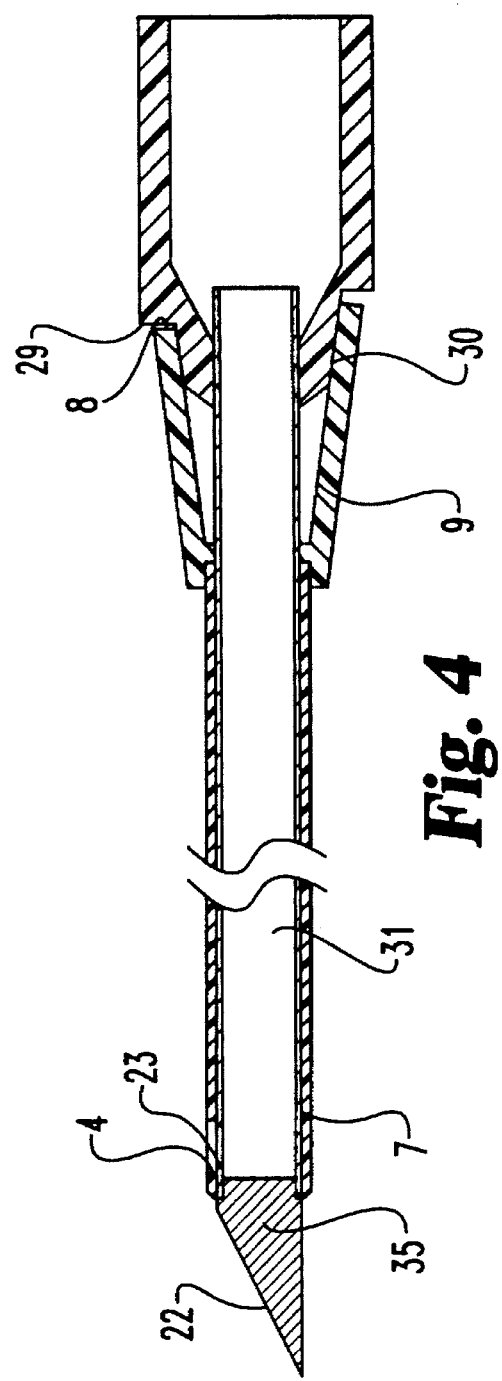

INTRAVENOUS CATHETER AND DELIVERY SYSTEM

FIELD OF THE INVENTION

This invention relates to catheters that are introduced into a cavity by needle, where proper positioning of the catheter is established by observation of fluid coming out of the needle.

DESCRIPTION OF THE PRIOR ART

There is a problem common among catheters introduced by needle into a cavity. That common problem is the uncertainty faced by the practitioner as to whether or not the catheter itself is properly inserted into the cavity. A major reason for this uncertainty is that the practitioner bases his judgment of proper insertion upon his observation of fluid flowing into a flash chamber. This observation does not always coincide with proper placement of the catheter. Often it is more related to placement of the needle tip, especially when a hollow needle tip is the source of fluid. In other cases, the problem may arise from a timing delay because the fluid passageways are too small to provide fluid to the flash chamber in a timely manner.

Various arrangements of needles and catheters have been proposed to solve these problems. One design uses a needle where fluid flows through a sharp, open tip, through the bore of the needle, and out a side hole of the needle into an annular flash chamber located between the catheter inner diameter and the needle outer diameter. Another design uses a solid needle with cutting edges where fluid flows into a circumferential groove adjacent the cutting edge, and then into a longitudinal groove along the outer diameter of the needle. In an alternative to that design, fluid flows into a side hole of the needle and down an internal bore. There are other designs, with either solid end or hollow end needles, where blood first flows into a groove or flat relief surface on the needle outer diameter, and then either along the groove or between the catheter and the flat relief. In all of these designs, the cylindrical wall of the catheter is not breached by any side hole.

SUMMARY OF THE INVENTION

The present invention concerns a catheter assembly design and method for ensuring proper insertion of a catheter into a cavity. One aspect of this invention concerns a needle with a solid tip and an internal passageway. The needle has a side hole that penetrates the wall of the needle near the solid tip and communicates with the internal passageway. The needle is received into the lumen of a close-fitting catheter. The catheter has one side hole near its insertion end which aligns with the needle side hole.

After the needle is inserted into the catheter, the assembly is positioned at the entry site with the side holes aligned and positioned away from the cavity wall. The sharp end of the needle is used to pierce the entry site. As the assembly is advanced into the cavity, cavity fluids will flow through the catheter side hole, through the needle side hole, into the needle internal passageway, and then into the chamber end of the needle. In a preferred embodiment, the needle and catheter contain complementary circumferential and axial alignment features that align their side holes in approximate concentricity. Insertion of the catheter assembly into a cavity results in fluid flowing into the chamber end of the needle only after the side hole of the catheter is located in the cavity.

It is an object of the present invention to provide a catheter assembly which is simple and economical to produce and which is compatible with other devices and methods commonly used by the practitioner.

It is another object of the present invention to provide a catheter assembly which facilitates proper placement of the catheter in a cavity.

It is another object of the present invention to reduce the possibility that the practitioner may unnecessarily pierce a second wall of the cavity.

These and other features and advantages will be apparent from the following description of the preferred embodiment of the invention.

BRIEF DESCRIPTION OF THE DRAWINGS

FIG. 3 is a top view of a catheter assembly of this invention, showing the needle of FIG. 2 inserted into the catheter of FIG. 1.

FIG. 4 is a sectional view of the catheter assembly of FIG. 3 taken along the line 4—4.

DESCRIPTION OF THE PREFERRED EMBODIMENT

Figure 1:
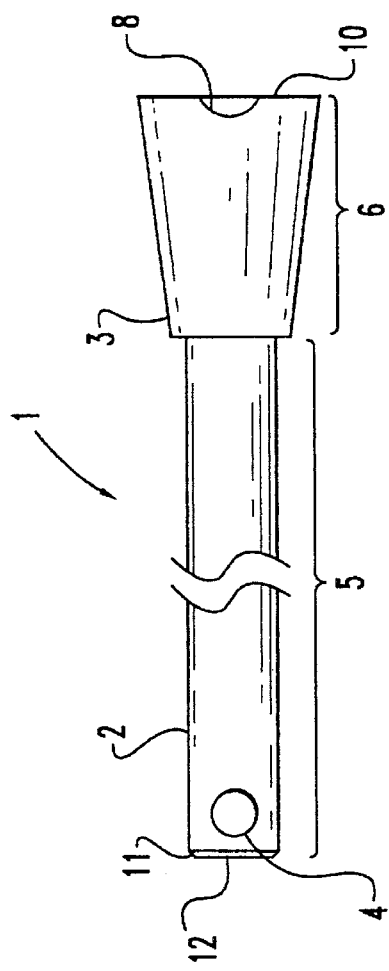
FIG. 1 is a top view of a preferred embodiment of a catheter useful in accordance with the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides a catheter assembly which permits the quick and reliable placement of a catheter into a body cavity, such as a vein. The placement is verified upon the observation of fluid, e.g., blood, in a flash chamber communicating with a needle received within the catheter being positioned. The catheter assembly has a fluid flow path that begins with a hole in the side of the catheter and continues through a side hole of the needle and from there to the flash chamber. The first entry of fluid into the needle therefore occurs when the side hole of the catheter comes into contact with fluid. Observation of fluid by the practitioner, and therefore positioning of the catheter, is based upon placement of the catheter side hole, and not the needle tip.

The preferred catheter assembly comprises a catheter 1 in which is received a closed-end needle 24. The catheter 1 of this invention is shown in FIG. 1. The catheter 1 has a distal, insertion end 2 and a proximal, base end 3. Located at the insertion end 2 is central opening 12 and first side hole 4. The catheter body 5 is cylindrical, and attached to a catheter hub 6 which is in the shape of a truncated cone. Insertion end 2 incorporates chamfer 11, which reduces trauma to the cavity upon insertion of the catheter. Base end 3 incorporates circumferential alignment feature 8 on end face 10.

Figure 2:
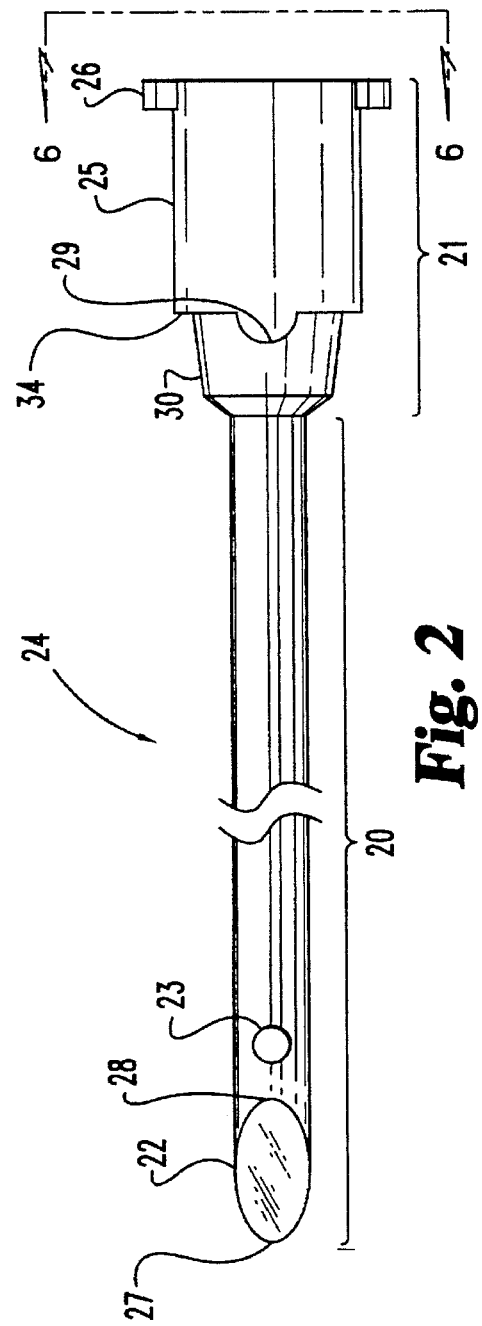
FIG. 2 is top view of a needle useful with the invention.

FIG. 2 shows a needle 24 useful with the invention. The needle 24 has a distal, sharp end 22, and a proximal, chamber end 25. The sharp end 22 has both a distal end 27 and a proximal end 28. Sharp end 22 is a solid, beveled tip, although other types of sharp tips, such as a diamond shape, can also work. The particular shape selected is a matter of choice and the invention is not restricted to any given design. Located near and axially aligned with the proximal end 28 is a side hole 23.

The needle 24 includes a needle body 20, which has a cylindrical outer shape except at the sharp end 22, and a needle hub 21. The needle hub 21 includes front face 34 and conical surface 30. Needle hub 21 also includes an attachment feature suitable for use with various connectors standard in the art. Depicted is a flange 26.

FIG. 3 shows the assembly of needle 24 into catheter 2. Chamber end 25 of the needle 24 and the base end 3 of the catheter 3 are aligned at one end of the assembly, sharp end 22 and insertion end 2 are aligned at the other end of the assembly, and side hole 23 and first side hole 4 are aligned. First side hole 4 is concentric with side hole 23.

Although a single side hole 23 in needle 24 is shown, a plurality of side holes at this approximate axial location could eliminate the need for a circumferential alignment feature to be discussed later. If more than one side hole has been put in needle 24, then alignment of the side holes with first side hole 4 of catheter 1 is more easily accomplished, and depends upon sufficient area of overlap and fluid communication.

The cut-away of FIG. 4 shows the alignment of chamber end 25 with base end 3. Conical surfaces 9 and 30 have a complementary design that provides both a fluid seal and axial alignment when chamber end 25 is inserted into base end 3. Front face 34 of needle 24 includes circumferential alignment feature 29. Alignment features 8 and 29 are complementary in design and provide circumferential alignment of chamber end 25 in base end 3. Although semicircular features have been shown as a means of accomplishing circumferential alignment, many other alignment features could be employed, including square, rectangular, triangular, and other geometric shapes. Circumferential alignment could also be accomplished by alignment of visual features of the needle and catheter. It is also possible to combine circumferential and axial alignment into a single feature.

FIG. 4 also shows the flow path for fluids from the cavity into the chamber end 25. Sharp end 22 of needle 24 first pierces into a cavity. Sharp end 22 pierces the cavity with first side hole 4 directed away from the cavity. As the practitioner continues to advance the catheter assembly into the cavity, fluid from the cavity is first able to enter the flow path at first side hole 4. The fluid continues to flow through side hole 23 and into internal passageway 31 of needle 24. Fluid continues to flow along internal passageway 31 to chamber end 25. The outer diameter of needle body 20 is approximately the same as the diameter of lumen 7 located within catheter 2. There is at most negligible flow between the outside of needle body 20 and the inside wall of catheter body 5. Fluid is not received at chamber end 25 unless it enters first side hole 4.

Figure 5:
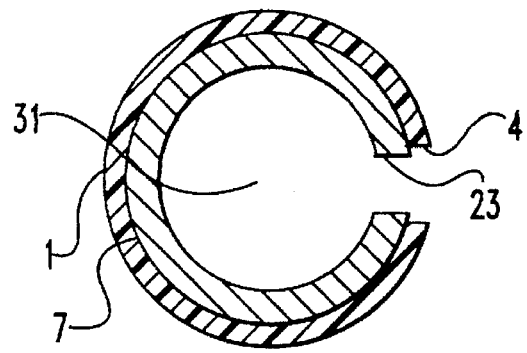
FIG. 5 is a sectional view of the catheter assembly of FIG. 3.

FIG. 5 shows the flow path from first side hole 4 through side hole 23 and into internal passaeway 31. First side hole 4 is preferably slightly larger than side hole 23 to account for inaccuracies in alignment.

Figure 6:
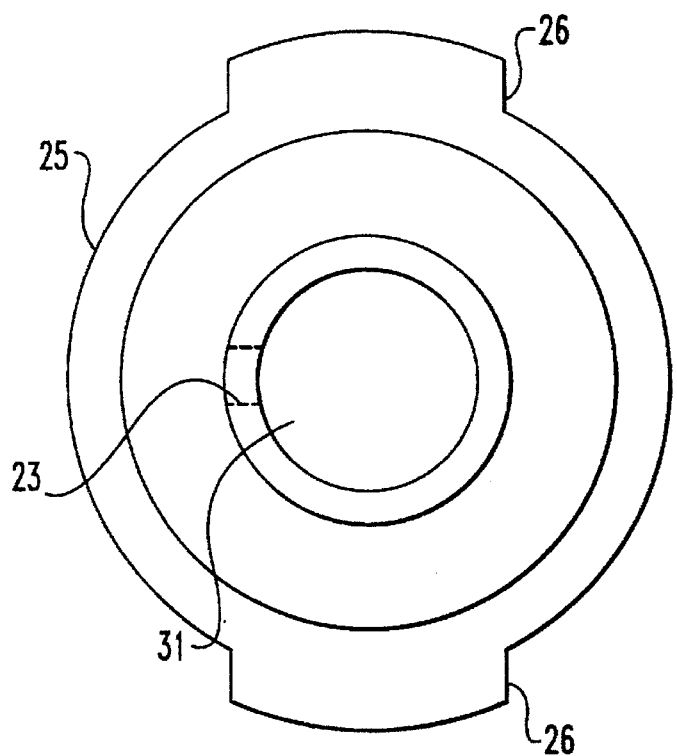
FIG. 6 is an end view of the needle of FIG. 2.

FIG. 6 is an end view of needle 24 and shows flange 26 provided for attachment of chamber end 25 to other equipment, such as flash chamber 40.

Figure 7:
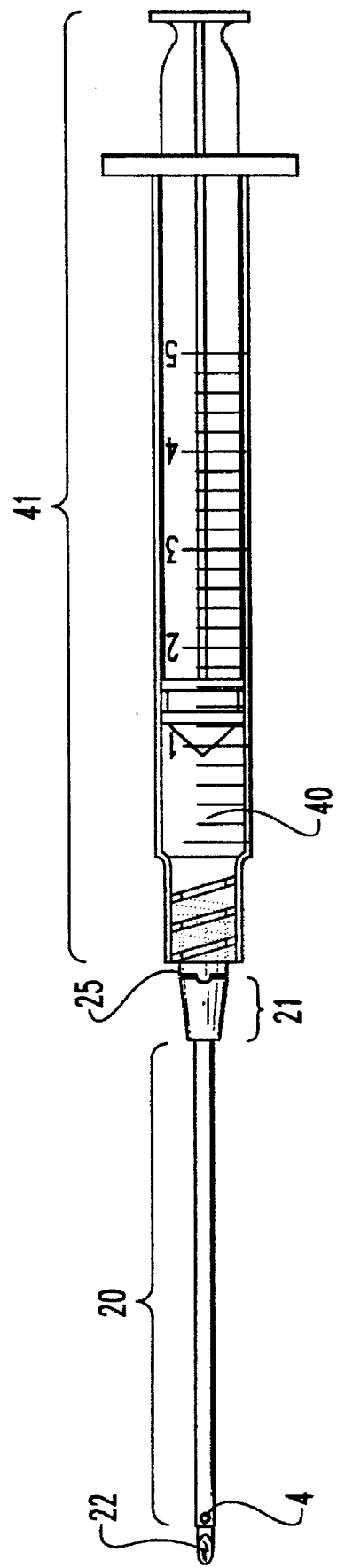
FIG. 7 is a view of the invention attached to a typical flash chamber.

FIG. 7 shows the catheter assembly connected to syringe 41 which contains flash chamber 40. Chamber end 25 of needle 24 is received with flash chamber 40.

Figure 8A:
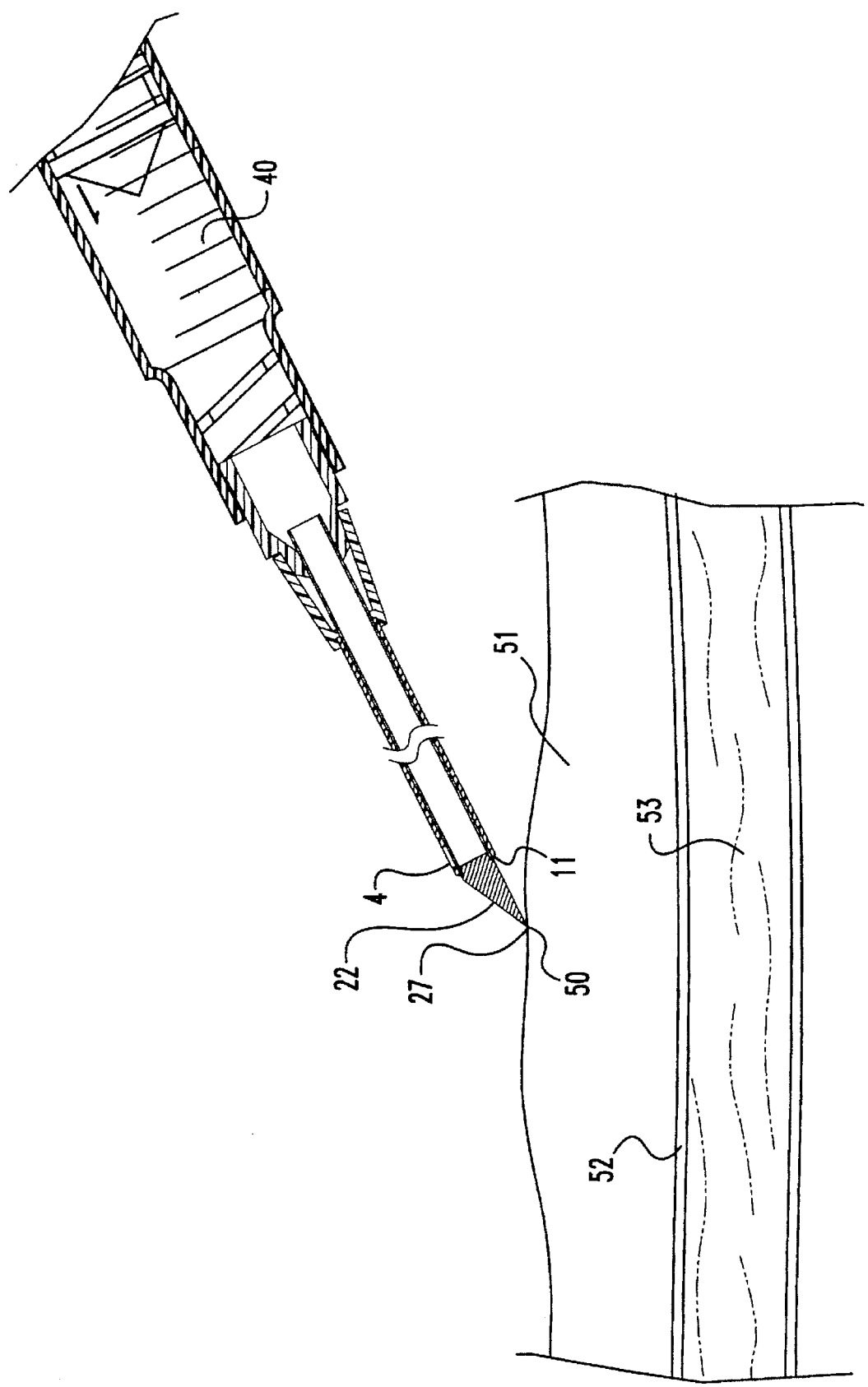
FIG. 8a shows the catheter assembly of FIG. 4 being placed at a site of entry.

FIG. 8a shows the catheter assembly, with flash chamber 40 in fluid communication therewith, positioned with tip 27 of needle 24 at site of entry 50 on skin 51. First side hole 4 of catheter 1 is directed away from vein cavity wall 52.

Figure 8B:
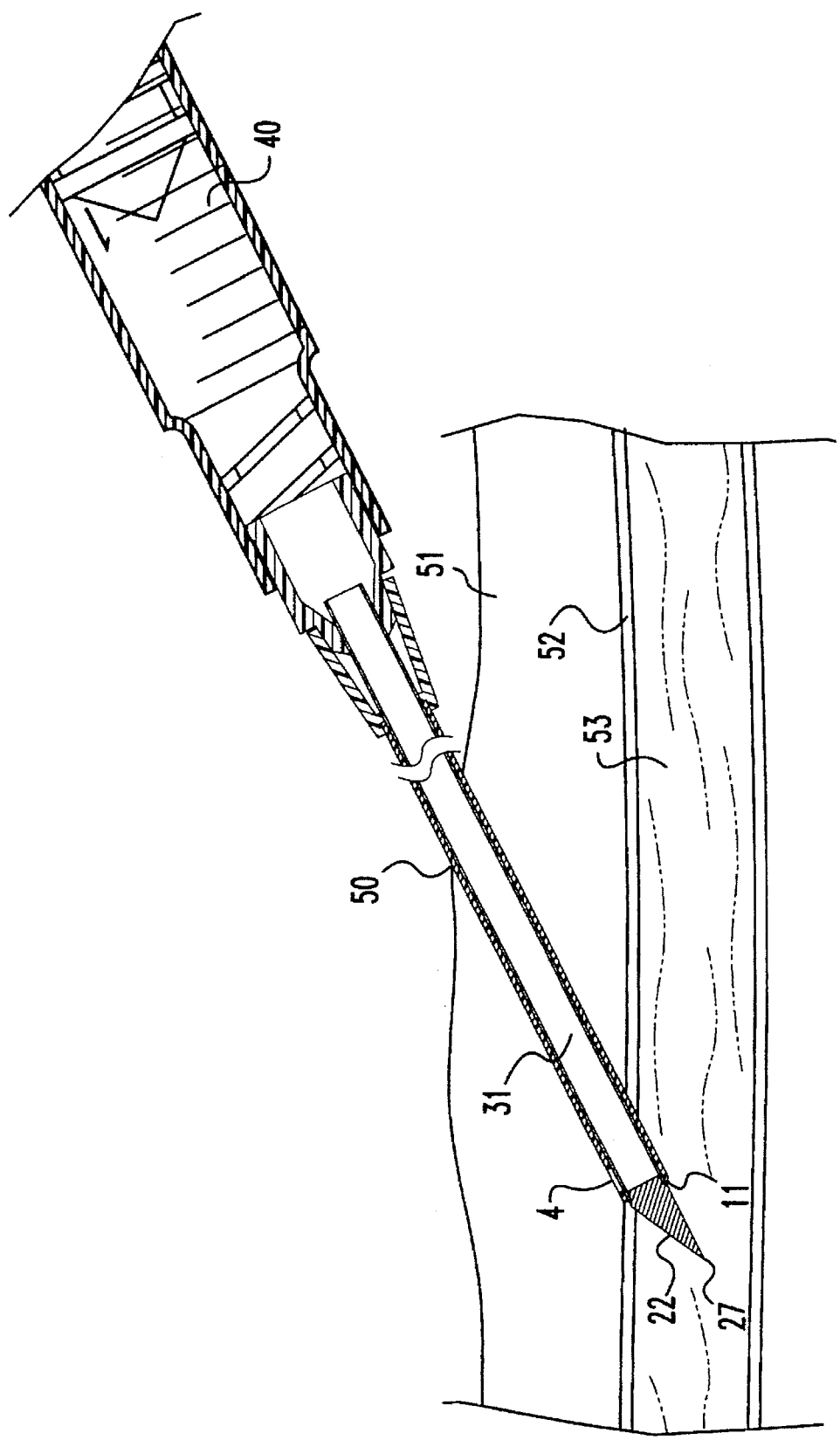
FIG. 8b shows the catheter assembly of FIG. 4 piercing a vein wall.

FIG. 8b shows the catheter assembly after it has been advanced through skin 51. Sharp end 22 of needle 24 has been advanced through vein wall 52. One region of chamfer 11 of catheter 1 has also advanced through vein wall 52, but first side hole 4 of catheter 1 has not advanced through vein wall 52. Blood 53 is not yet flowing into internal passageway 31.

Figure 8C:
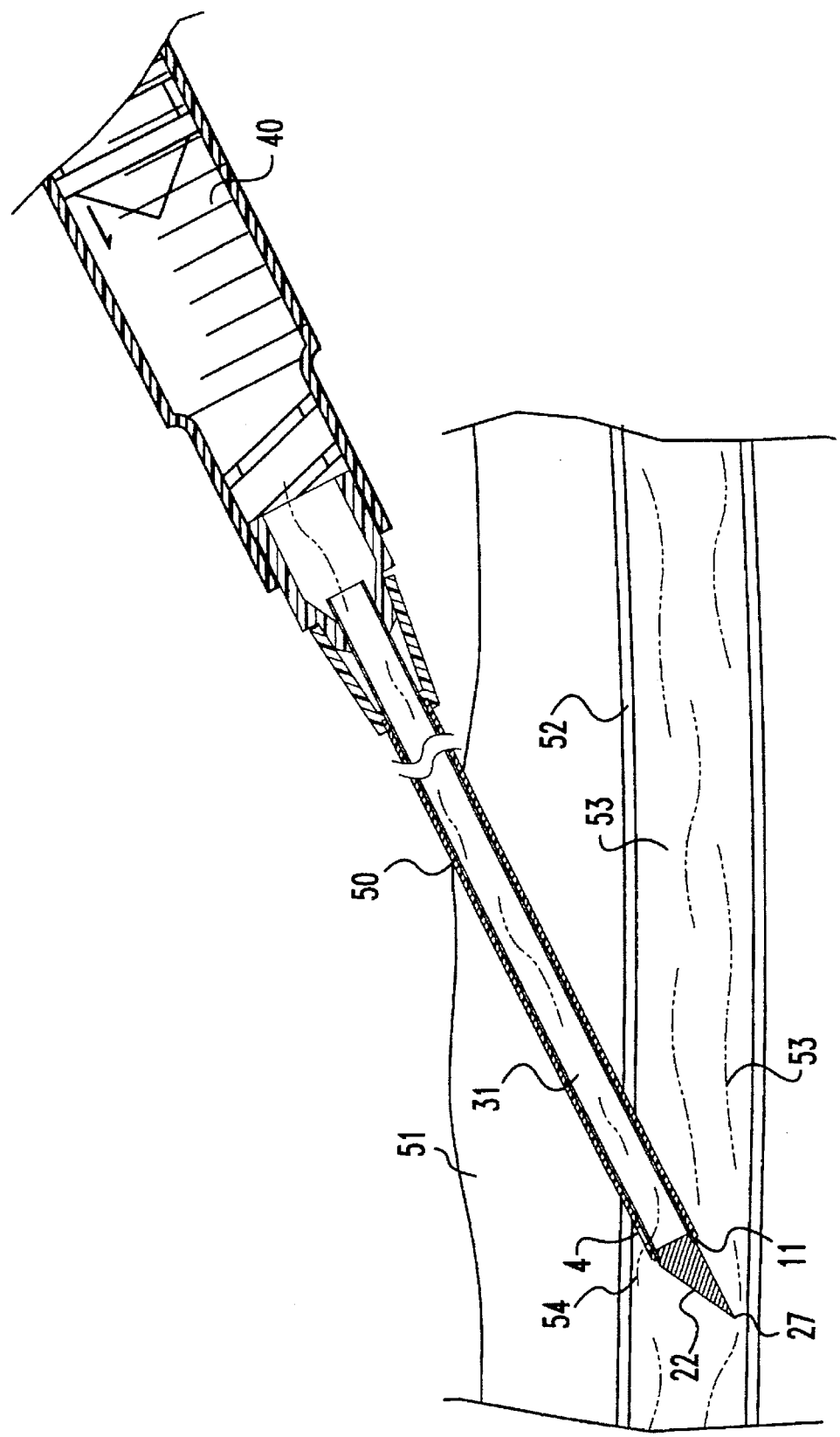
FIG. 8c shows the catheter assembly of FIG. 4 being located within a vein and blood flowing into the catheter assembly flow path.

FIG. 8c shows the catheter assembly after further insertion through vein wall 52. First side hole 4 is in fluid communication with blood 53. Blood 53 is flowing into internal passageway 31 and into flash chamber 40. First side hole 4, and also side hole 23 of needle 24, are large enough that fluid flows quickly into flash chamber 40. Quick flow gives timely notification of proper insertion to the practitioner, and reduces the possibility that the practitioner may unnecessarily advance the assembly and pierce another wall of the cavity.

Figure 8D:
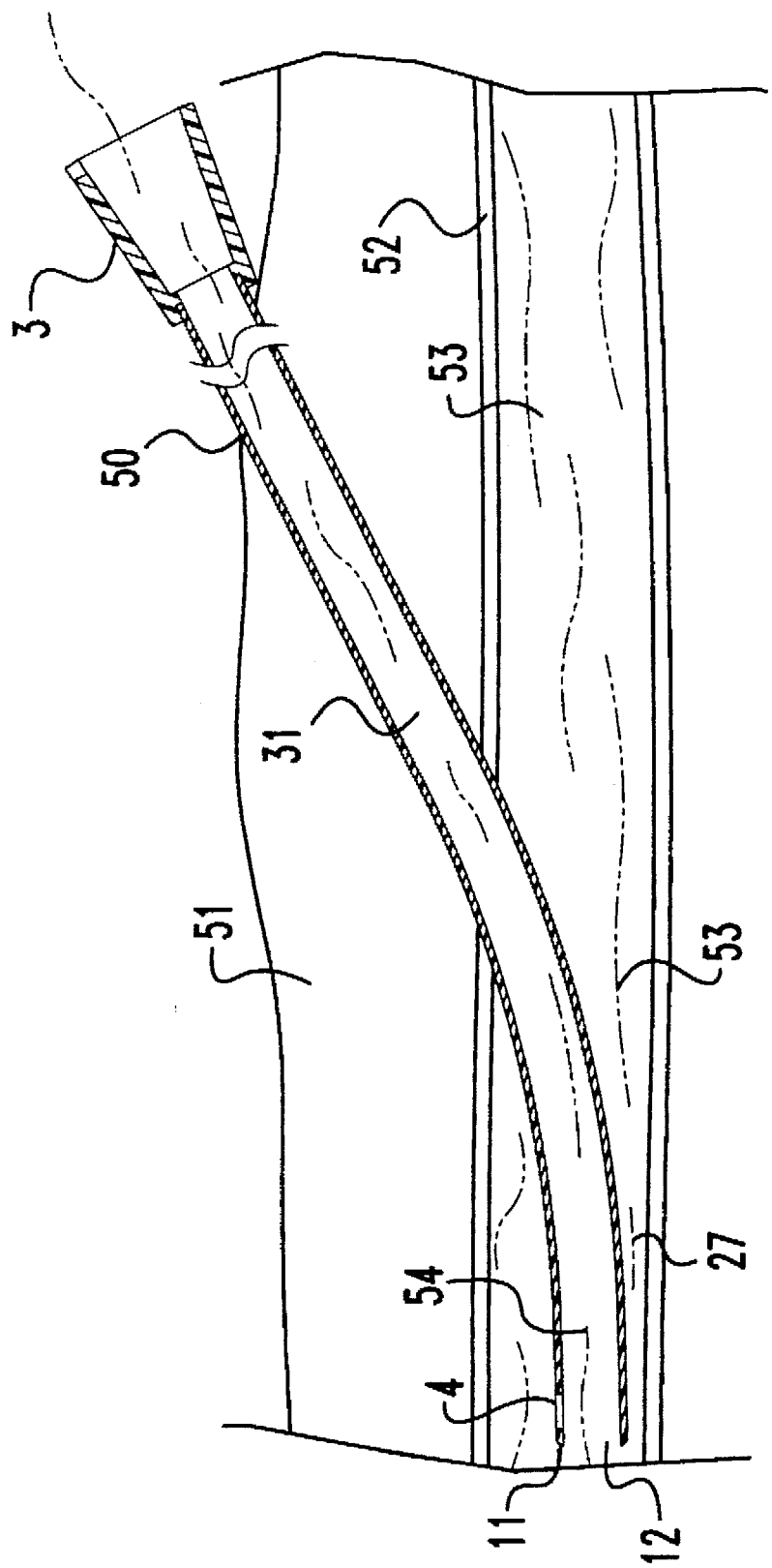
FIG. 8d shows the catheter remaining within a vein after the needle has been removed.

FIG. 8d shows catheter 1 inserted through vein wall 52. Needle 24 and flash chamber 40 are removed. Blood 53 can flow through both first side hole 4 and also central opening 12. Another device can be attached to base end 3 of catheter 1.

Figure 8E:
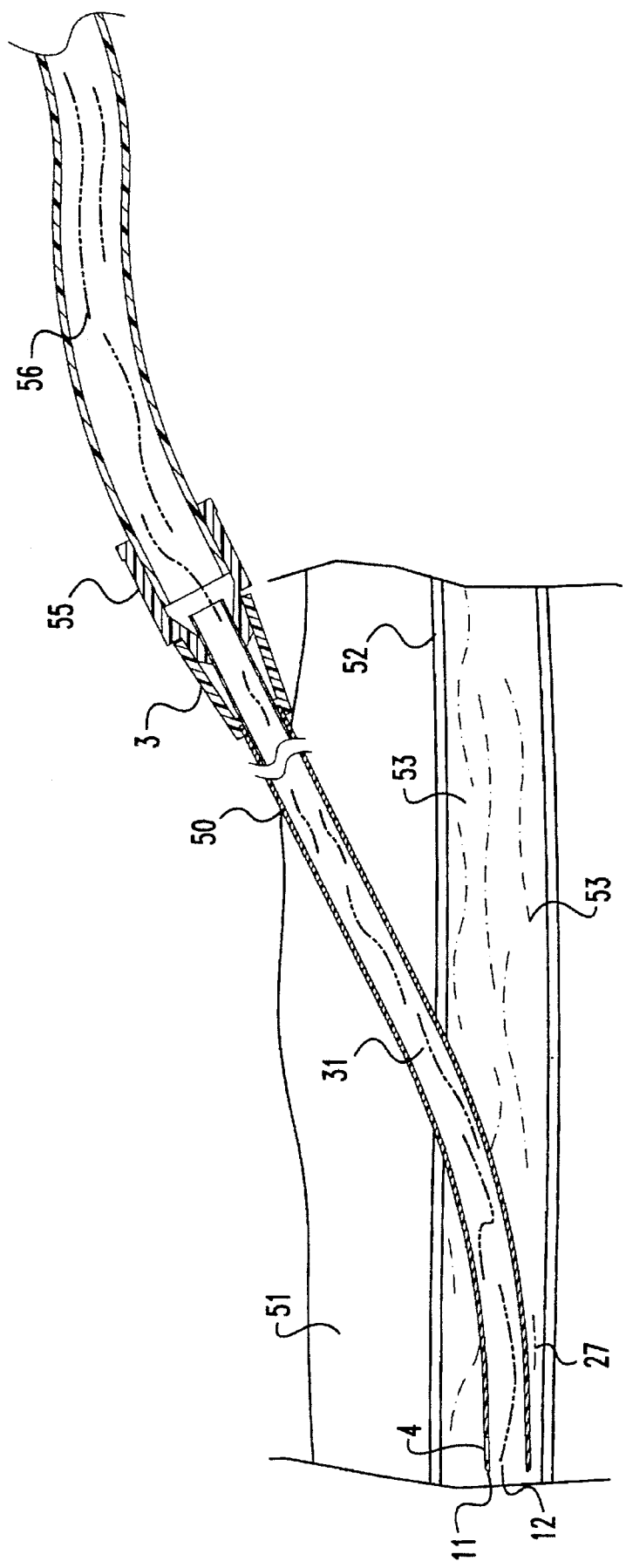
FIG. 8e shows the catheter of FIG. 8d as attached to a standard infusion set.

FIG. 8e shows catheter 1 with standard infusion set 55 attached to base end 3. Fluid 56 is being delivered into blood 53 via catheter 1.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A catheter assembly which comprises:

a catheter having a distal, insertion end and a proximal, base end, said catheter defining an internal lumen having a diameter and being open through the insertion end and base end, said catheter containing a first side hole adjacent to the insertion end, the first side hole being in fluid communication with the lumen; and a needle received within the lumen of said catheter, said needle having a sharp, distal end and a proximal, chamber end, said needle defining an internal passageway closed at the sharp end and open through the chamber end, said needle having an outer diameter approximately the same as the diameter of the lumen of said catheter, said needle defining a side hole adjacent to the sharp end and in fluid communication with the internal passageway, said needle and catheter having a first position with the sharp end of said needle extending outwardly beyond the distal and of said catheter and with the side hole of said needle being in fluid communication with the side hole of said catheter.

2. The catheter assembly of claim 1 wherein the sharp end of said needle is beveled.

3. The catheter assembly of claim 1 wherein said needle has only one side hole adjacent to the sharp end.

4. The catheter assembly of claim 1 wherein the chamber end of said needle and the base end of said catheter include means for axial alignment of said needle and said catheter in the first position.

5. The catheter assembly of claim 1 wherein the chamber end of said needle and the base end of said catheter include means for circumferential alignment of said needle and said catheter in the first position.

6. The catheter assembly of claim 1 wherein a flash chamber suitable for viewing fluid received from the first side hole of said catheter is in fluid communication with the chamber end of said needle.

7. The catheter assembly of claim 4 wherein the chamber end of said needle and the base end of said catheter include means for circumferential alignment of said needle and said catheter in the first position.

8. A method for introducing a catheter through a cavity wall and into a cavity comprising the following:

(a) providing a catheter having a distal, insertion end and a proximal, base end, said catheter defining an internal lumen having a diameter and being open through the insertion end and base end, said catheter containing a first side hole adjacent to the insertion end, the first side hole being in fluid communication with the lumen;

a needle received within the lumen of said catheter, said needle having a sharp, distal end and a proximal, chamber end, said needle defining an internal passageway closed at the sharp end and open through the chamber end, said needle having an outer diameter approximately the same as the diameter of the lumen of said catheter, said needle defining a side hole adjacent to the sharp end and in fluid communication with the internal passageway, said needle and catheter having a first position with the sharp end of said needle extending outwardly beyond the distal end of said catheter and with the side hole of said needle being in fluid communication with the side hole of said catheter; and a flash chamber in fluid communication with the chamber end of said needle and suitable for viewing fluid that has flowed out of the chamber end of said needle;

(b) positioning the catheter assembly at a site of entry for the cavity wall with the side holes directed away from the cavity wall;

(c) piercing through the cavity wall at the site of entry with the sharp end of the needle; and (d) advancing the catheter assembly until fluid is seen to flow into the flash chamber.

9. The invention of claim 8 wherein the method includes:

(e) removing the needle from said catheter assembly.

10. The method of claim 8 wherein the sharp end of said needle is beveled.

11. The method of claim 8 wherein said needle has only one side hole adjacent to the sharp end.

12. The method of claim 8 wherein the chamber end of said needle and the base end of said catheter include means for axial alignment of said needle and said catheter in the first position.

13. The method of claim 8 wherein the chamber end of said needle and the base end of said catheter include means for circumferential alignment of said needle and said catheter in the first position.

14. The method of claim 12 wherein the chamber end of said needle and the base end of said catheter include means for circumferential alignment of said needle and said catheter in the first position.

15. The catheter assembly of claim 8 in which the cavity is a vascular cavity.

* * * * *